US011536666B2

(12) United States Patent
Aksoy et al.

(10) Patent No.: US 11,536,666 B2
(45) Date of Patent: Dec. 27, 2022

(54) MATRICES FOR DETECTING VOLATILE ORGANIC COMPOUNDS

(71) Applicant: Auburn University, Auburn, AL (US)

(72) Inventors: Burak Aksoy, Auburn, AL (US);
Zhihua Jiang, Auburn, AL (US);
Mediha Aksoy, Auburn, AL (US);
Benjamin Beck, Auburn, AL (US);
Navid E. Alamdari, Auburn, AL (US)

(73) Assignee: Auburn University, Auburn, AL (US)

( * ) Notice: Subject to any disclaimer, the term of this patent is extended or adjusted under 35 U.S.C. 154(b) by 113 days.

(21) Appl. No.: 17/095,127

(22) Filed: Nov. 11, 2020

(65) Prior Publication Data

US 2021/0140893 A1    May 13, 2021

Related U.S. Application Data

(60) Provisional application No. 62/933,783, filed on Nov. 11, 2019.

(51) Int. Cl.
*G01N 21/80* (2006.01)
*G01N 21/78* (2006.01)
*G01N 33/02* (2006.01)
*G01N 33/12* (2006.01)
G01N 31/22 (2006.01)

(52) U.S. Cl.
CPC .......... *G01N 21/80* (2013.01); *G01N 21/783* (2013.01); *G01N 33/02* (2013.01); *G01N 31/221* (2013.01); *G01N 33/12* (2013.01)

(58) Field of Classification Search
CPC ........ C12Q 1/04; G01N 21/78; G01N 21/783; G01N 21/80; G01N 31/221; G01N 31/223; G01N 33/02; G01N 33/12; Y10T 436/173845; Y10T 436/175383
USPC ... 436/20, 21, 111, 113, 163, 164, 166, 169; 422/400, 401, 402, 420, 425, 430
See application file for complete search history.

(56) References Cited

U.S. PATENT DOCUMENTS

| 3,206,317 | A | 9/1965 | Golber |
| 3,496,066 | A | 2/1970 | Berger |
| 4,129,483 | A | 12/1978 | Bochner |
| 4,925,789 | A | 5/1990 | Edberg |
| 6,387,650 | B1 | 5/2002 | Townsend |
| 2015/0241412 | A1* | 8/2015 | Hakovirta ............... C12Q 1/10 435/38 |
| 2021/0396730 | A1* | 12/2021 | Zhang ............... G01N 33/0047 |

FOREIGN PATENT DOCUMENTS

| KR | 20160105653 A | 9/2016 |
| WO | 2014014894 A2 | 1/2014 |

OTHER PUBLICATIONS

Pirsa et al. Polym. Adv. Technol., vol. 29, pp. 2750-2758, 2018.*
Alamdari et al. Taianta, vol. 224, 121913, pp. 1-12, Nov. 23, 2020.*
Cai et al.: "Determination of total volatile basic nitrogen (TVB-N) content and Warner-Bratzler shear force (WBSF) in pork using Fourier transform near infrared (FT-NIR)spectroscopy", Food Chemistry, vol. 126, Issue 3, Jun. 1, 2011, pp. 1354-1360, available at: https://doi.org/10.1016/j.foodchem.2010.11.098.
Z. Dang, The investigation of carboxyl groups of pulp fibers during kraft pulping, 5 alkaline peroxide bleaching, and TEMPO-mediated oxidation, (2007).
Guo et al., "Portable Food-Freshness Prediction Platform Based on Colorimetric Barcode Combinatorics and Deep Convolutional Neural Networks", Advanced Materials, 2020.
Hakovirta et al. "Self-assembled micro-structured sensors for food safety in paper based food packaging", Apr. 22, 2015, Published by Elsevier B.V., Materials Science and Engineering C, available at: http://dx.doi.org/10.1016/j.msec.2015.04.020.
X. Huang, et al.,Modification of Na-bentonite by polycations for fabrication of amphoteric semi-IPN nanocomposite hydrogels, Appl. Clay Sci. 42 (2009) 455-459.
Idakwo et al. "Total volatile base nitrogen (TVBN) and trimethylamine (TMA) content of "Bunyi youri" as influenced by the addition of glucose and clove during storage", International Journal of Biotechnology and Food Science vol. 4(5), pp. 81-85, Dec. 2016, available at http://www.sciencewebpublishing.net/ijbfs.
Jeon et al. (2002), Chitosan as an edible invisible film for quality preservation of herring and Atlantic cod, J. Agric. Food Chem. (2002). https://doi.org/10.1021/jf011693I.
Navid Etebari Alamdari et al., "A novel paper-based and PH-sensitive intelligent detector in meat and seafood packaging", Nov. 23, 2020, Published by Elsevier B.V.
J.Madejová, et al., Benefits of near-infrared spectroscopy for characterization of selected organo-montmorillonites, Vib. Spectrosc. 57 (2011) 8-14.
J.W. Odom, M.B. Koné, Elemental analysis procedures used by the Auburn University Department of Agronomy and Soils, (1997).
Saito et al. (2007) "Cellulose Nanofibers Prepared by TEMPO-Mediated Oxidation of Native 20 Cellulose," Biomacromolecules, 8(8):2485-2491.
Salfinger and Tortorello (Eds.), "Compendium of Methods for the Microbiological Examination of 25 Foods, Fifth Ed." © 2015, American Public Health Association, ISBN 978-0875532738.
Sasser, Myron "Bacterial Identification by Gas Chromatographic Analysis of Fatty Acid Methyl Esters (GC-FAME)", MIDI, May 1990.
International Search Report and Written Opinion dated Jan. 21, 2021, by the ISA-EPO for application No. PCT/US2020/059987.

* cited by examiner

*Primary Examiner* — Maureen Wallenhorst
(74) *Attorney, Agent, or Firm* — Christopher M. Scherer; Joseph T. Leone; DeWitt LLP (57) ABSTRACT

A device for detecting volatile compounds. The device includes a substrate and a matrix disposed on the substrate. The matrix includes a carboxyl-rich binder, a clay, and a pH-sensitive indicator dye admixed with the binder and the clay. The pH-sensitive indicator dye is dimensioned and configured to change color in response to contact with a pre-determined concentration of a volatile compound.

19 Claims, 7 Drawing Sheets

MATRICES FOR DETECTING VOLATILE ORGANIC COMPOUNDS

CROSS-REFERENCE TO RELATED APPLICATIONS

Priority is hereby claimed to provisional application Ser. No. 62/933,783, filed Nov. 11, 2019, which is incorporated herein by reference.

BACKGROUND

Meat-based food products are notoriously well known to spoil quickly, even when properly stored in a refrigerator just above freezing (e.g., 4° C.). Meats commonly consumed throughout the industrialized world, such as beef, pork, chicken, and fish are susceptible to rapid spoilage by cryophilic microorganisms (also known as psychrophilic microorganisms). These are spoilage microorganisms, typically bacteria or fungi, which thrive at refrigeration temperatures. As a result, these meat products, even when properly handled and stored, have relatively short shelf-lives at temperatures above 0° C. The shelf-life of meat products is directly related to the initial concentration of contaminating organisms present in the meat at the time it is sold or distributed to the consuming public.

The sources of microbial contamination in food are many and varied. These sources include (among many others) unsanitary agricultural or processing conditions, insufficiently low temperatures during transportation and pre- and post-sale storage, defective packaging, and intentional adulteration food using unapproved ingredients by unscrupulous producers.

There are many conventional methods for measuring the concentrations of bacterial contamination in meat-based food products. See, for example, Salfinger and Tortorello (Eds.), "Compendium of Methods for the Microbiological Examination of Foods, Fifth Ed." © 2015, American Public Health Association, ISBN 978-0875532738. But these methods are laboratory methods requiring specialized equipment and skills. Additionally, many of the assays require 24 to 48 hours of incubation time in a temperature-controlled incubator before the results can be determined. Many of the methods also require a solid nutrient base to support the growth of individual pathogenic cells into bacterial colonies. Even with a century or more of effort, many food-borne pathogenic bacteria are difficult or impossible to incubate into colonies by artificial means.

There have been attempts to measure the bacterial concentration in food by measuring specific metabolic by-products of individual microorganisms. These methods include, for example, electrical impedance assays, ATP assays, antibody-based assays, and carbon-14 radio-labelled substrate assays. Colorimetric methods have also been described. See, for example, Golber, U.S. Pat. No. 3,206,317, issued Sep. 14, 1965, which describes an indicating device for refrigerated food packaging. The device uses a nutrient medium that will support the growth of pathogenic microorganisms. The nutrient medium is inoculated with a small portion or aliquot of the same food that is being packaged. The nutrient medium includes a reduction-sensitive indicator dye. (Examples of indicators that change color in the presence of pH changes associated with microbial growth include phenol red, bromocresol blue, and neutral red.) The dye is responsive to reducing agents generated by microorganisms present in the food. Growth of bacteria in the aliquot of food indicates microbial growth in the larger mass of the packaged food.

See also Berger et al., U.S. Pat. No. 3,496,066, which describes a similar approach wherein the metabolic activity of contaminating bacteria induce a colorimetric change in a dye or dye precursor, such as tropinones and dioxanes. Bochner, U.S. Pat. No. 4,129,483, describes using a non-biodegradable substance (tetrazolium) which is chemically reduced to produce a detectable color change in response to bacterial growth.

Edberg, U.S. Pat. No. 4,925,789, describes a selective growth medium for a microbe containing a nutrient indicator which can only be metabolized by a target microbe. When metabolized by a target microbe, the nutrient indicator releases a moiety which imparts a detectable change to the medium.

See also Townsend et al, U.S. Pat. No. 6,387,650, issued May 14, 2020. This patent describes a method for detecting the existence or measuring the concentration of total viable bacteria in a test sample from a food product. Here, a medium is provided which contains three or more different enzyme substrates each having a nutrient moiety and a detectable moiety linked together. When a substrate is hydrolyzed by a bacterial enzyme to create a separate detectable moiety, it causes or produces a detectable signal. The substrates produce detectable signals when any one of a phosphatase enzyme, a glycosidase enzyme or a peptidase enzyme, presumably from a bacterial source, is present in the medium.

Even in the most technologically advanced cultures of the world, or perhaps "especially" in the most technically advanced cultures, meat spoilage remains a continuing threat to public health. Recalls of huge quantities of tainted meat products produced and packaged in large-scale plants have become increasingly common in the United States. For example, in 2008, in the face of massive sanctions and threatened criminal action from the federal government, the Hallmark/Westland Meat Packing Company of Chino, Calif. voluntarily recalled more than 143 million pounds of potentially tainted raw ground beef. In 2011, Cargill Meat Solutions Corporation was the focus of a recall of more than 35 million pounds of ground turkey due to *Salmonella* contamination. The tainted ground turkey was responsible for one death and the sickening of over 90 people. In 2015, Cargill recalled over 1 million pounds of ground beef tainted with *E. coli*.

The aggregate economic consequences (to farmers and ranchers, processors, distributors, and consumers alike) are also vast. People around the globe are not inclined to take chances with their food. Except in dire of circumstances, humans of all cultures adopt a "better safe than sorry" attitude when it comes to food safety. As a result, it has been estimated that globally about 1.3 billion tons per year of the edible portion of food raised for human consumption is discarded due to obvious spoilage or suspicions of spoilage.

There thus remains a long-felt and unmet need for a method of determining, quickly and without specialized equipment, whether meat-based foods are safe to consume.

SUMMARY

Disclosed herein is a device for detecting volatile compounds. The device comprises a substrate and a matrix disposed on the substrate. The matrix comprises a binder comprising carboxyl-rich biomass, a clay, and a pH-sensitive indicator dye admixed with the binder and the clay. The pH-sensitive indicator dye is dimensioned and configured to change color in response to contact with a pre-determined concentration of volatile compounds.

In preferred versions of the device, the clay comprises a smectite clay, an illite clay, a phyllosilicate, or a combination of these. The preferred clay comprises bentonite. The binder comprises carboxyl-rich biomass, which can be derived from any source, without limitation. Acid-treated soybean hulls are the preferred carboxyl-rich biomass for the binder. But other fruit and vegetable peels, pea pods, nut shells, beet pulp, and the like can be used with commensurate success. In one version of the device, the binder comprises nanofibrillated biomass, preferably derived from nanofibrillated soybean hulls.

The substrate is a material is preferably paper, due to its low cost and ease of processing. Other substrate material may also be used, including thermoplastic films, thermosetting films, and cellulosic films.

Any suitable pH sensitive dye may be used, without limitation. A host of such dyes are known and available commercially. Preferred pH-sensitive indicator dyes for testing meat spoilage are Bromocresol Purple, dichlorofluorescein, Methyl Red, Bromocresol Green, and Chlorophenol Red.

Also disclosed herein is a method of using the detector described for testing the spoilage of food. The method comprises providing a detector as described herein, wherein the pH-sensitive indicator dye is dimensioned and configured to change color in response to a concentration of total volatile base nitrogen compounds generated by spoilage microorganisms growing within a food product. The change in color of the pH-sensitive indicator dye thus occurs at or below a threshold concentration of spoilage microorganisms within the food product at which the food product is deemed unsafe to consume by humans. The detector is then placed in a package of food. Monitoring the device for a change of color indicates that the food inside the package has spoiled and should not be eaten.

DETAILED DESCRIPTION

Abbreviations and Definitions:

The following abbreviations and definitions are used throughout the specification and claims. Words and phrases not given an explicit definition are to be defined as understood in the field of food science.

Bentonite is a clay comprising crystalline clay minerals belonging to the smectite group, which are hydrous aluminum silicates containing iron and magnesium as well as either sodium (sodium bentonite) or calcium (calcium bentonite). As used herein the word "bentonite" designates all types of bentonite. Calcium bentonites sometimes referred to as fuller's earth. Bentonite of various grades and particle sizes can be obtained commercially from a host of suppliers. In the working examples described herein, "CSP 1"- and "CRD 0"-brand bentonites obtained commercially from Carco Mineral Resources, Inc. (San Antonio, Tex., U.S.A.) were used.

The term "carboxyl-rich biomass" refers to the organic materials produced by plants and animals. Common sources of carboxy-rich biomass include (without limitation): (1) agricultural wastes/or byproducts, such as corn stalks, straw, seed hulls, sugarcane leavings, bagasse, nutshells, soybean hulls and peapods, and the like; (2) woody materials, such as wood or bark, sawdust, timber slash, and mill scrap; (3) municipal waste, such as waste paper and yard clippings; and (4) energy crops, such as poplars, willows, switch grass, alfalfa, prairie bluestem, corn, soybean.

Bromocresol purple=5',5"-dibromo-o-cresolsulfophthalein, a triarylmethane dye. It is colored yellow below about pH 5.2, and violet above about pH 6.6. In its cyclic sulfonate ester form, it has a pKa value of 6.3, and is usually prepared as a 0.04% aqueous solution:

CFU=colony-forming units.

The word "clay" is used herein broadly and in its commonly understood meaning to designate an abundant, naturally occurring, fine-grained inorganic material composed predominantly of hydrous aluminum silicates. As used herein, the word "clay" explicitly encompasses kaolin, ball clays, fire clays, sodium bentonite, calcium bentonite (fuller's earth), and common clays.

Illite is a group of closely related non-expanding clay minerals. Illite is a secondary mineral precipitate, and an example of a phyllosilicate, or layered alumino-silicate. Its structure is a 2:1 sandwich of silica tetrahedron (T)-alumina octahedron (O)-silica tetrahedron (T) layers. The space between this T-O-T sequence of layers is occupied by poorly hydrated potassium cations which are responsible for the absence of swelling. Structurally, illite is quite similar to muscovite with slightly more silicon, magnesium, iron, and water and slightly less tetrahedral aluminium and interlayer potassium. The chemical formula is given as $(K,H_3O)(Al,Mg,Fe)_2(Si,Al)_4O_{10}[(OH)_2(H_2O)]$, but there is considerable ion substitution.

Nanofibrillated biomass can be made from carboxyl-richbiomass, such as soybean hulls (for example) using commercial pulverizing/grinding equipment. Here, soybean hulls were converted to nanofibrillated fiber using a Masuko "Supermasscolloider"-brand grinder. (Masuko Sangyo Co. Ltd., 1-12-24 Honcho, Kawaguchi, Saitama, Japan 332-0012.)

Meat=any food product for human or non-human consumption comprising animal-derived proteinaceous material, without limitation. "Meat" thus includes (but is not limited to) food products comprising or derived from bovines (e.g., beef), porcines (pork), ovines (lamb, mutton, goat), birds of all description (e.g., chickens, turkeys, pheasants, etc.) fish of all description, shellfish, cephalopods (e.g., octopus, squid, cuttlefish, and the like), game birds (quail, partridge, ducks, geese) and game animals (deer, rabbits, elk, etc.), and marine mammals, whether domesticated or wild.

Phyllosilicates are any silicate mineral clay having the tetrahedral silicate groups linked in sheets, each group containing four oxygen atoms, three of which are shared with other groups so that the ratio of silicon atoms to oxygen atoms is two to five. Phyllosilicates include, but are not limited to baileychlore (zinc iron aluminum magnesium silicate hydroxide), chamosite (iron magnesium aluminum silicate hydroxide oxide), chlorite, clinochlore, (iron magnesium aluminum silicate hydroxide), cookeite (lithium aluminum silicate hydroxide), nimite (nickel magnesium iron aluminum silicate hydroxide), pennantite (manganese aluminum silicate hydroxide), penninite (iron magnesium aluminum silicate hydroxide) sudoite (magnesium aluminum iron silicate hydroxide), glauconite (potassium sodium iron aluminum magnesium silicate hydroxide), illite (hydrated potassium aluminum magnesium iron silicate hydroxide), kaolinite (aluminum silicate hydroxide), montmorillonite (hydrated sodium calcium aluminum magnesium silicate hydroxide), palygorskite (hydrated magnesium aluminum silicate hydroxide), pyrophyllite (aluminum silicate hydroxide), sauconite (hydrated sodium zinc aluminum silicate hydroxide), talc (magnesium silicate hydroxide), and vermiculite (hydrated magnesium iron aluminum silicate hydroxide).

SBH=soybean hulls. NFSBH=nanofibrillated soybean hulls.

Smectite clays are mineral clays having the 2:1 structure of mica and vermiculite, but with a lower charge per formula weight, roughly about 0.6 to about 0.2. As in vermiculite, the interlayer in smectite clays contains exchangeable cations. Smectites include, but are not limited to montmorillonite, beidellite, and nontronite. All are dioctahedral, but they differ in the composition of the tetrahedral and octahedral sheets. Smectites do not fix $K^+$ as readily as do vermiculites because smectites have a lower layer charge, but smectites swell more extensively than vermiculite.

Spoilage microorganisms refers to any microbial or fungal contaminate in meat that contributes to the spoliation of the meat.

TCC=total colony count.

TEMPO-oxidized cellulose nanofibers are native wood celluloses converted to individual nanofibers 3-4 nm wide that are at least several microns in length (i.e., aspect ratios >100) using TEMPO (2,2,6,6-tetramethylpiperidine-1-oxyl radical)-mediated oxidation and successive mild disintegration in water. See, for example, Saito et al. (2007) "Cellulose Nanofibers Prepared by TEMPO-Mediated Oxidation of Native Cellulose," *Biomacromolecules,* 8(8):2485-2491.

TVB-N=total volatile basic nitrogen.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth.

All references to singular characteristics or limitations disclosed herein shall include the corresponding plural characteristic or limitation, and vice-versa, unless otherwise specified or clearly implied to the contrary by the context in which the reference is made. The indefinite articles "a" and "an" mean "one or more."

All combinations of method or process steps as used herein can be performed in any order, unless otherwise specified or clearly implied to the contrary by the context in which the referenced combination is made.

The methods and compositions of matter disclosed herein can comprise, consist of, or consist essentially of the essential elements and limitations of the method or composition described herein, as well as any additional or optional ingredients, components, or limitations described herein or otherwise useful in detecting spoilage in food products generally and protein-containing food products specifically.

Food Spoilage Generally:

Fish spoilage occurs in storage mainly as a result of microbial activity. The composition of fish flesh (and all meat products for that matter) make it favorable for microbial growth. Keeping fish fillets in a refrigerator at 4° C. to maintain freshness cannot completely inhibit the growth of cryophilic spoilage microorganisms; they are capable of thriving at refrigerator temperatures.

Figure 1:
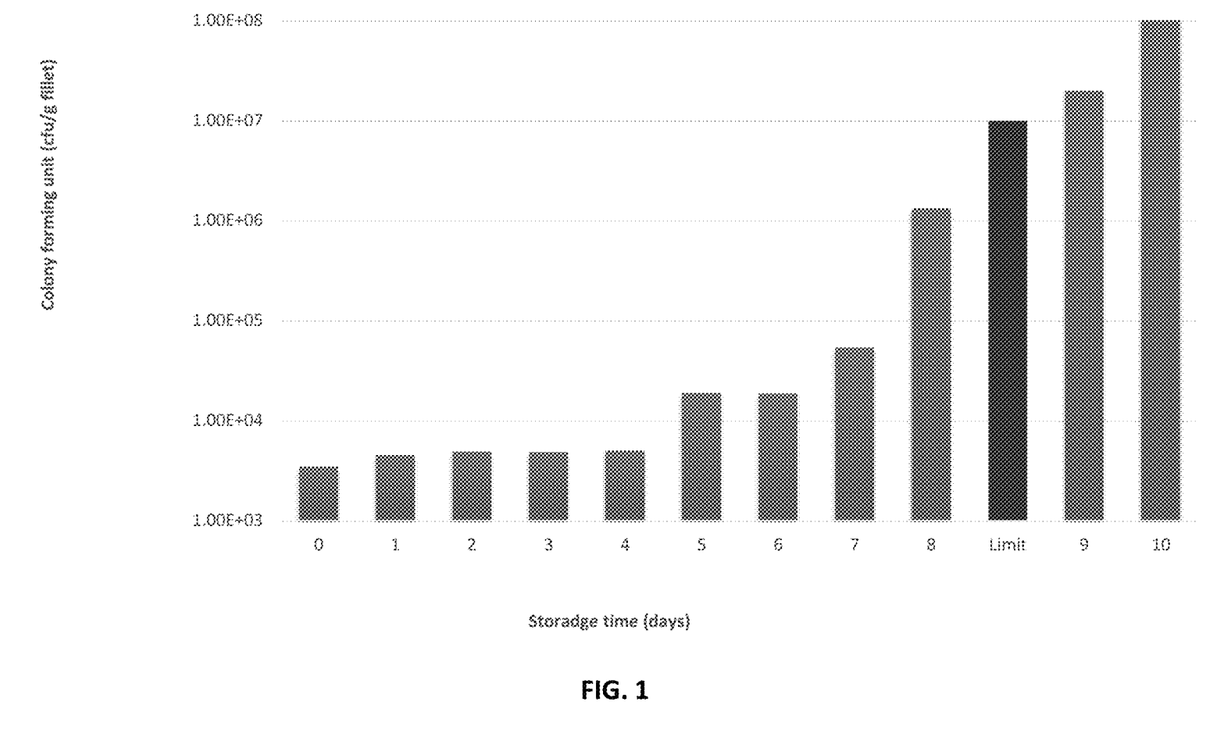
FIG. 1 is a histogram showing daily total aerobic plate count (log CFU/g) of catfish fillet samples stored at 4° C. The maximum permissible limit for consumption in the United States is 7.0 $\log_{10}$ CFU/g, represented by the red column.

FIG. 1 tabulates the results of simple spoilage experiment. A sample of newly killed fish (catfish) chilled to 4° C. was immediately tested for bacterial load. As shown in the far left entry of FIG. 1, a low bacterial load (as measured by total colony count (TCC); 3.68 $\log_{10}$ cfu/g) was obtained at the start of the storage period. The TCC remained low during the first four (4) days of storage. A slow increase in TCC values was observed from Day 5 to Day 7. As shown in FIG. 1, though, after Day 7 a rapid increase in TCC was observed. The TCC value on Day 9 exceeded the maximal permissible limit of 7.0 $\log_{10}$ cfu/g (column in red), considered as the upper acceptable limit for fish destined for human consumption (per the U.S. Department of Agriculture). The microbial analysis confirmed that an acceptable concentration of bacteria is maintained for the first eight (8) days of storage. By Day 9, though, the reject limit for TCC was reached. The fish was no longer fit for human consumption due to the high concentration of bacteria.

Colorimetric Detection Based on Total Volatile Basic Nitrogen (TVB-N):

Disclosed herein is a colorimetric method and corresponding composition of matter for detecting meat spoilage. The method is based on detecting the amount and/or concentration of total volatile basic nitrogen (TVB-N) produced by spoilage organisms growing within the meat product.

TVB-N is an indicator of the freshness of meat. TVB-N compounds principally comprise ammonia ($NH_3$), dimethyl amine ($H—N—(CH_3)_2$) and trimethyl amine ($N—(CH_3)_3$). TVB-N is conventionally expressed as mg nitrogen/100 g of muscle tissue. See, for example, Cai et al. (2011) "Determination of total volatile basic nitrogen (TVB-N) content and Warner-Bratzler shear force (WBSF) in pork using Fourier transform near infrared (FT-NIR) spectroscopy," *Food Chemistry* 126(3):1354-1360 and Idakwo et al. (2016) "Total volatile base nitrogen (TVBN) and trimethylamine (TMA) content of "Bunyi youri" as influenced by the addition of glucose and clove during storage," Int'l J. of Biotech. and Food Sci. 4(5):81-85. These volatile, basic amines are produced via the metabolic breakdown of amino acid by the food spoilage microorganisms in the spoiled meat. TVB-N compounds are responsible for the characteristic odor associated with spoiled meat and fish. Conventionally, these compounds are assayed spectrophotometrically. See the above-cited references.

Disclosed herein is a method for detecting spoilage of meat using a colormetric detector comprising a pH-sensitive indicator dye embedded into or disposed onto a substrate. The treated substrate is then placed into close proximity with the meat being tested for spoilage organisms. Preferably the treated substrate is placed into the same sealed package with the meat. It need not be in direct contact with the meat, but it can be. It must be in the same enclosed space or in communication with the enclosed space in which the meat is situated so that TVB-N generated by microorganisms growing within the meat can reach the detector. When the concentration of TVB-N compounds emanating from the meat product is sufficiently high, the TVB-N compounds induce a visible color change in the detector via a pH change driven by the TVB-N. That is, the color change of the detector is a direct result of the basicity of the TVB-N. The concentration of the TVB-N in the space surrounding the meat is, in turn, a direct result of the metabolism of spoilage microorganisms within the meat sample.

The pH sensitivity of the dye is calibrated so that a color change occurs when TCC of spoilage microorganism within the meat has reached a threshold point deemed unsafe for human consumption. The threshold point itself is largely irrelevant, and may be set at the whim or desire of the processor or packager. However, in most countries, the threshold "unsafe" level of microbial contamination in meat (as measured by TCC or other means) is set by law. Meat having a TCC level higher than the threshold level is thus legally defined as unsafe for human consumption. The detector described herein can be calibrated empirically to change color at a point where the desired, preset threshold level has been reached or exceeded. This is done by way of a conventional standard curve or calibration curve that measures the concentration of the spoilage microorganisms in a meat sample using an industry-accepted assay. (See "Compendium of Methods for the Microbiological Examination of Foods, Fifth Ed.," supra.) The calibration curve is then used empirically to fabricate a detector using a pH-sensitive dye that changes color at the TVB-N concentration corresponding to the point in the calibration curve where the meat has met (or is dangerously close to) the threshold "unsafe" level of microbial contamination.

The preferred pH-sensitive indicator dye for use in the method and composition of matter is bromocresol purple, which is yellow at about pH 5.2 and below, and turns to purple at about pH 6.6 and above. Other pH-sensitive dyes having a color change within a similar pH range may also be used. A host of such pH-sensitive dyes are known and include, but are not limited to dichlorofluorescein (pH≤4.0 (colorless)-pH≥6.6 (green)), Methyl Red (pH≤4.2 (pink)-6.2 (yellow)), Bromocresol Green/Methyl Red (pH≤4.6 (pink)-pH≥5.2 (blue/green)), and Chlorophenol Red (pH≤5.2 (yellow)-pH≥6.8 (red)). Suitable pH-sensitive dyes can be purchased commercially from a host of international suppliers, including Sigma-Aldrich (a wholly owned subsidiary of Merck KGaA), St. Louis, Mo., USA.

The preferred detector is constructed of a matrix comprising a binder (preferably made from soybean hull ("SBH") and a clay pigment. The pH-sensitive dye described in the immediately preceding paragraph is then admixed into or deposited onto the matrix. The resulting matrix is then deposited onto a suitable carrier or substrate. The nature of the substrate is not critical, so long as it is inexpensive and sufficiently robust to hold the matrix. For example, the substrate may be a thermoplastic or thermosetting film, or a cellulosic film. The substrate may be made from paper.

Working Example—Preparation and Fabrication of Detectors

Binder Production:

To produce the coating binder, course ground soybean hulls (SBH) were purchased from Republic Mills, Inc., Ohio, USA, and processed through the following method developed at the Alabama Center for Paper and Bioresource Engineering (AC-PABE), Auburn University, Auburn, Ala.

Soybean Hull (SBH) Binder:

SBH was mixed in an acidic water medium (using concentrated hydrochloric acid (HCl) (Assay: 36.5-38%) at an elevated temperature and atmospheric pressure, followed by mechanical treatment using a high mixing mode of a Ninja® professional 72 Oz. Blender. The proposed production steps are cost-effective, scalable, and effluent-free.

NFSBH Binder:

The acid-treated SBH was further processed mechanically, by passing through a Masuko Ultra-fine grinder "Supermasscolloider" MKZA10-15IV, (Masuko Sangyo Co., Ltd., Japan) to produce NFSBHs. A total number of twelve passes and two different stones were used to reach the desired level of defibrillation (Stone 1: made of aluminum oxide, mesh 80, four passes; Stone 2: made of aluminum oxide and silica, mesh 40, eight passes).

Coating Formulation and Preparation:

Coatings are constructed from three components: pH-sensitive dye (1 part), pigment (bentonite, 100 parts), and binder (25/10 parts for SBHs/NFSBHs). BCP, a detector with a distinct color change from yellow to purple (pH range of 5.2-6.8), was used as a TVBN detector.

CSP-1 Bentonite was provided by CARCO Mineral Resources, Inc. and exploited as the pigment in the present study.

Bentonite and BCP were mixed with SBH or NFSBH binder using a high-shear lab disperser (White Mountain Process, USA) set to a mixing speed of 2000 RPM and kept mixing for providing complete homogeneity of the coating material. Water was added to the mixture to reach the desired viscosity for coating.

Fabrication of the Detectors:

Fabrication of detectors was done by applying the prepared homogenous coating materials on Whatman No. 2 filter papers using the drawdown rod coating method. The coated papers were immediately dried by blowing hot air.

Two sets of detectors were prepared using either processed SBH or NFSBH as the binder. Each set consists of twelve detectors with different initial pH values. This was done by adjusting the pH of each set of coating materials to values between 0.25 and 5.2 by concentrated HCL or 5 M NaOH before applying on the filter paper (#1: 0.25, #2: 0.50, #3: 0.75, #4: 1.00, #5: 1.50, #6: 2.00, #7: 2.50, #8: 3.00, #9: 3.50, #10: 4.00, #11: 4.50, and #12: 5.20). Thus, a total of 24 detector samples were prepared and tested.

Coating formulations comprised of bromocresol purple (BCP), biodegradable and low-cost soybean hulls (SBH) and bentonite were developed and then be coated on a filter paper using a conventional drawdown rod coating method, which has excellent scalability for commercial-scale fabrication in paper mills.

The preparation of a homogenous, foam-free, and well-mixed coating formulation is the pre-requisite for the fabrication of coated paper-based detectors. To achieve this goal, the coating components were mixed thoroughly using a high-shear disperser. The agitation of the coating mixture under high agitation is possible by substituting the conventional paper coating binders such as PVOH. Traditional paper coating binders usually form stable foams when mixed vigorously, causing inhomogeneity and pin-holes in the applied coating. Furthermore, there is no report of applying an agricultural waste, byproduct, or residue in the polymer matrix in food quality detectors. Hence, the full utilization of processed SBH provides improved processability while reducing the overall cost of the detector production and represents a unique approach to the development of meat spoilage detectors.

Morphology of the Detectors:

Scanning Electron Microscopy (SEM) was used to analyze the morphology and structure of detectors. To be able to capture images of better resolution and quality and to avoid the electron buildup on the surface of the sample, it is necessary to make them conductive before testing by SEM. For this purpose, the detector was attached to the SEM sample stub using double-sided tape, and Pelco SC-6 sputter coater was used to gold coat the samples by applying plasma on their surface for one minute. The SEM microscope (JSM 7000F FESEM, JEOL Inc., USA) was used for image processing at 20 kV and magnifications of 500×, 2000×, and 5000×.

Elemental Analysis:

Elemental analysis of bentonite was conducted according to the following procedure. Approximately 0.50-10 g dried solid samples were weighed, transferred into ceramic crucibles, and kept overnight in a muffle furnace at 500° C. Samples were then allowed to cool and digested on a hot plate at ~168° C. using 1N Nitric Acid and 1N Hydrochloric Acid. Cooled samples were filtered with Whatman No. 1 filter paper and brought to volume in 100 ml volumetric flask using deionized water. Solutions were analyzed by Inductively Coupled Plasma Optical Emission Spectroscopy (Vista-MPX ICP-OES Radial Spectrometer, Varian Inc., USA) calibrated with standard concentrations of the desired elements. J. W. Odom, M. B. Koné, Elemental analysis procedures used by the Auburn University Department of Agronomy and Soils, (1997).

The functional and physical properties of bentonite, such as swelling and stability in saline solution, are significantly dependent on counter-ion valence and surface charge. The metal ion content of the bentonite used here shows its sodium content is almost 1.4 times the calcium content, making it a Na-bentonite. The Na-bentonite has a higher swelling capacity, providing higher viscosity in suspensions and a greater state of disaggregation, comparing with Ca-bentonite, and improved BCP adsorption as well as larger interlayer space for SBH intercalation.

TABLE 1

| Elemental Analysis of Bentonite | |
|---|---|
| Metal content of bentonite | ppm (average of duplicate tests) |
| Phosphorus | <0.1 |
| Potassium | 1814 ± 31 |
| Calcium | 9460 ± 140 |
| Magnesium | 4550.5 ± 131.5 |
| Iron | 4603 ± 148 |
| Manganese | 239.5 ± 4.5 |
| Boron | 4.75 ± 0.05 |
| Copper | 10.9 ± 0.8 |
| Zinc | 33.65 ± 2.25 |
| Aluminum | 8863.5 ± 261.5 |
| Sodium | 12879 ± 182 |
| Silica | 252 ± 20 |

Study of the Morphology by SEM:

An SEM image of the detector at 500× (data not shown) confirms that the coating mixture is successfully coated on the surface of the filter paper in a homogeneous manner while having enough space between particles for gas penetration. The available interlayer space between pure bentonite platelets is larger than that of the bentonite particles in the detector.

Functional Groups:

Structural properties of the fabricated detector, SBH binder, untreated SBHs, and bentonite were investigated using Nicolet 6700 FT-IR spectrometer coupled to OMNIC™ Software, Thermo Scientific, USA. The transmittance of the detector surface was plotted against wavenumber (400-4000 cm−1) in Attenuated Total Reflection (ATR) infrared mode, 64 scans, and resolution of 4 $cm^{-1}$.

Further structural properties of the detector were revealed by FT-IR (data not shown). Acid treatment of SBHs at high temperature contributes to solubilizing and activating of pectin and hemicellulose and increasing the number of available free carboxylic acid groups, as by the increased intensity of the corresponding spectral band (from 1637.29 $cm^{-1}$ to 1641.15 $cm^{-1}$).

FT-IR revealed a significant reduction in hydroxyl bands' intensity, indicating transient water loss and a reduced number of available water molecules to form hydrogen bonding as a result of drying as the last stage in the detector manufacturing process. The bound water loss could result in interlayers collapsing and Na+ cations entering the hexagonal cavities. In addition to the heating effect, these changes in hydroxyl bands can also be attributed to the intercalation of bentonite interlayer spaces.

All bentonite-specific peaks were present in the detector spectra with decreased intensities and a slight downward or upward frequency shifts, confirming some structural changes in the bentonite particles during detector manufacturing. The Si—O out-of-plane vibration band (1002.82 $cm^{-1}$) is reported to be the most sensitive spectral band to thermal and chemical treatments, and its frequency shift reflects the change in the environment of Si—O band due to the presence of alkyl chains of organic compounds, intercalation of the polymer within the clay galleries, and acid or heat treatment. See J. Madejová, et al., Benefits of near-infrared spectroscopy for characterization of selected organo-montmorillonites, Vib. Spectrosc. 57 (2011) 8-14; and X. Huang, et al., Modification of Na-bentonite by polycations for fabrication of amphoteric semi-IPN nanocomposite hydrogels, Appl. Clay Sci. 42 (2009) 455-459.

Binder Properties:

SBH binder properties rely on pectin and both hemicellulose and protein rich components yielded by the acid treatment. To evaluate the effect of the developed processing method on the binding ability of SBH, carboxylic acid and protein content of the SBHs was evaluated before and after the treatment.

Carboxylic Acid Group Content:

The carboxylic acid group content of the SBH samples was determined using the conductometric titration method. Briefly, air-dried samples of SBH equivalent to 1.5 g oven-dry were added to 300 ml of 0.10 N HCl and stirred for one hour. The pulp was then filtered and washed with deionized water until the effluent water conductivity was less than 5 µScm−1. The washed pulp was treated with a 0.001 N NaCl (250 ml) and 0.10 N HCl solution (1.5 ml), stirred and titrated with 0.05 N NaOH in an atmosphere of nitrogen. Titration was done using Metrohm Autotitrator, consisting of an 856 Conductivity module connected to the main module (888 Titrando) coupled with Tiamo™ 2.5 software. The conductivity was plotted against the volume of NaOH resulting in a parabolic curve composed of three distinguishable decreasing, constant, and increasing zones. The carboxylic acid group content of the samples was then determined based on the intersections of the three trend lines drawn for each of these zones.

SBH was evaluated for their carboxylic acid group and protein content before and after acid treatment and the results are reported in Table 2. There is a significant increase, approximately two times, in carboxylic acid group content in the acid-treated SBH, i.e., SBH binder, which can be one of the most important factors in the improvement of binding properties of SBHs by providing stronger hydrogen binding affinity compared to the hydroxyl groups. Carboxylic acid groups carry a negative charge at acidic medium and can have electrostatic interactions with metal cations of bentonite's interlayer space. This leads to a charge imbalance in the interlayer space, which can be neutralized by adsorption of ammonia. Other than the electrostatic interactions, surface interactions can also happen between hydroxyl groups in silicate layers and the hydroxyl- or carboxyl-functional groups of SBH, leading to further bonding of SBHs and bentonite. In addition to the above-mentioned contribution of carboxylic acid groups to the formation of coating matrix, they enhance attachment of the coating mixture onto the paper substrate by making hydrogen bonds with hydroxyl groups of paper's cellulose fibers.

In the current study, binder nanofibrillation is done by Masuko microfluidizer to enhance physical and functional properties. The higher aspect ratio of nanofibrillated cellulose (NFC) compared to cellulose fibers improves the mechanical properties of the coating layer through the composed tight interfiber entanglements. Furthermore, NFC intertwines with the paper fibers, providing strong bonding between the coating layer and paper substrate. The major drawback of mechanical methods for nanofibrillation is the high energy consumption. Modification of fibers by chemical pretreatment before the mechanical defibrillation is usually done by incorporating oxidizing agents such as 2,2,6,6-tetramethylpiperidine-1-oxyl (TEMPO), which introduce negatively-charged functional groups, minimize aggregation of fibers and reduce defibrillation intensity. The carboxylation is of great importance for producing NFC from wood pulps, because the carboxyl group of these fibers are usually low (ranging from as low as 1 mmol/100 g for unbleached hardwood to 25 mmol/100 g for peroxide bleached hardwood). Z. Dang, The investigation of carboxyl groups of pulp fibers during kraft pulping, alkaline peroxide bleaching, and TEMPO-mediated oxidation, (2007).

However, these oxidation processes are mostly limited to the lab-scale due to the high cost of the oxidizing agents. The high carboxylic acid group content of SBH (43.75 mmol/100 g), which reaches to an even higher value (86.23 mmol/100 g) with a simple one-stage hot acid pretreatment, has a potential to make the nanofibrillation process of SBHs more economically viable and commercially feasible. The prevention of cellulose fibers aggregation in the present study is probably due to the emergence of pectin- and hemicellulose-coated fiber surfaces, causing repulsive forces between fibers. Besides, unlike the long fibers of wood pulps, which can cause clogging in high-pressure homogenizing systems like microfluidizers, the SBH fibers are short to start with, and acid treatment leads to the removal of amorphous regions present in the cellulose structure, reducing the fiber length to even lower values. The increase in carboxylic group content can also be attributed to the solubilizing, activation, and availability of the carboxylic-rich components (mainly pectin) by combined mechanical and acid treatment.

TABLE 2

Carboxylic Acid Group and Protein Content of untreated SBHs and SBH binder

| Sample | Carboxyl Content (mmol/100 g)* | Protein Content (%)* |
| --- | --- | --- |
| Untreated SBHs | 43.75 ± 0.32 | 12.46 ± 0.08 |
| SBH Binder | 86.23 ± 2.86 | 9.74 ± 0.03 |

*Average of duplicate analysis

Protein Content:

Protein was measured by the combustion method using a TruMac Nitrogen Analyzer (Leco Corporation, St. Joseph, Mich., USA). Briefly, pre-weighed samples (2 g) in duplicate were dropped into a high-temperature furnace (1100° C.) and flushed with pure oxygen for very rapid combustion. Any atmospheric gases that have entered during the sample loading were purged prior to the combustion. The result of the percent nitrogen content of samples was calculated using a typical protein factor of 6.25 (N×6.25). Ethylenediaminetetraacetic acid (EDTA) was used as a standard. K. Helrich, Official methods of analysis, 15th ed., Association of Official Analytical Chemists (AOAC) Arlington, Va., Arlington, Va., 1990.

Microbiological Analysis:

The aerobic bacterial growth in fish samples was quantified by determination of TVC to correlate the trend and timing of color change with the microbial population. Also, the type of bacterial species responsible for fish spoilage was characterized.

Fish Sample Preparation and Storage Conditions:

Two samples of channel catfish (*Ictalurus punctatus*), each averaging 1.5 kg, were obtained from the USDA-ARS, Aquatic Animal Health Research Unit, Auburn, Ala. The fish fillet was immediately removed and washed with sterile water and was cut aseptically into similar size pieces and mixed to obtain homogenous samples. The fillets were immediately sampled (day 0) and analyzed in duplicate for microbial analysis. Remaining fillets were divided into groups under sterile conditions for detector evaluation and microbial count per sampling time points, in duplicate. Samples were kept in sealed Petri dish with parafilm, and all samples were then stored at 4° C.

Determination of TVC:

Bacterial growth was also performed in parallel to the above detector evaluation trial, stored in the same conditions and tested simultaneously on a daily basis. The test was done according to the method described by Jeon et al. (2002), Chitosan as an edible invisible film for quality preservation of herring and Atlantic cod, J. Agric. Food Chem. (2002). https://doi.org/10.1021/jf0116931., with a slight modification. Daily, 5 g of fish fillet sample was transferred aseptically to a stomacher bag and diluted 1:1 with a physiological saline peptone solution (PPS; 0.85% NaCl, 0.1% peptone). The mixture was homogenized for 2 min using a stomacher (Seward Laboratory Stomacher 80, England) to yield a stock solution from which successive dilutions were prepared. Tenfold serial dilution of each sample (in duplicate) were then prepared in PPS, and 0.1 ml of serially diluted samples were immediately plated onto plate count agar (PCA) plates. After two days of growth at 28° C., the total viable colonies were counted and reported as colony-forming units (CFU) per gram of fish.

Identification of Spoilage Bacteria:

Bacterial isolates were identified by gas chromatography (GC) analysis of their fatty acid methyl ester (FAME) profiles using the MIDI microbial identification system (MIDI, Newark, Del.). The extraction procedure outlined in the Sherlock MIS operating manual (version 4.5) was used to obtain FAMEs for GC analysis of cellular fatty acid profiles. Five colonies, representative of the variability in shape, color, and size of all colonies on the plate, were selected. These colonies were separately plated into TBS plates and incubated overnight at 28° C. Overnight culture of 25-30 mg of bacteria was harvested and placed in 13-mm 100-mm glass tubes. Bacterial cells were saponified in 1 ml of NaOH and methanol solution while boiling in a water bath for 30 min. After cooling, the fatty acids were methylated in 2 ml of HCl and methanol reagent for 10 min in an 80° C. water bath. Then, the FAMEs were extracted in hexane and methyl tert-butyl ether (1.25 ml). Any residual fatty acids and reagents were removed from the organic extract by washing with 3 ml of a 0.3 M sodium hydroxide solution for 5 min. Finally, the top ⅔ phase was removed and transferred to GC vial, and FAMEs were injected into an Agilent Technology 6850 gas chromatograph for analysis by the RCLN50 method. FAMEs were identified by comparison of their retention times with those of authentic standards obtained from Microbial ID, Inc. (Newark, Del., USA). FAMEs in hexane were used as calibration standards. M. Sasser, Bacterial identification by gas chromatographic analysis of fatty acids methyl esters (GC-FAME), Newark, N.Y. Microb. ID. (2006).

Sensory Response Evaluation:

The fabricated detectors were exposed to fish samples or ammonium hydroxide solution to test their response to the volatile basic compounds.

Effect of Detector's pH and Packaging Conditions:

The colorimetric response of the fabricated detectors with different initial pH values (0.25-5.20) upon exposure to the volatile basic compounds generated by fish during storage as a result of progressive decay of meat freshness was evaluated. Also, for investigating the effect of fish weight and headspace volume on detector response, duplicate samples of fillets (60 g or 120 g each) were placed in a sterile Petri dish (150 mm×15 mm or 100 mm×15 mm) with the detectors (cut to circles with a diameter of 15 mm) inside the top of the lid in triplicate. The detector responses were visually observed and photographed daily for ten days.

Durability:

Based on the real-time monitoring of the colorimetric response of detectors and their correlation with fish spoilage, detectors of optimum pH were selected and further analyzed for their durability to determine how long the color change remains visible on the detector after exposure to a certain amount of ammonia vapor. For this purpose, detectors were cut to squares (2.7 cm×2.7 cm), which covered each of the wells of the microtiter plates and exposed them to 100 μL of 5 mM ammonium hydroxide solution (made from a 28-30% NH4OH). Typically, meat and fish packages are kept under refrigeration during transportation and storage, but sometimes temperatures can become higher than 4° C. Therefore, to simulate real-life conditions, the durability of detectors was tested by attaching them to the lid of microtiter plates kept at 4° C. as well as room temperature. Photographs of samples were taken immediately after the initial color change, every hour until 12th hour, and every 12 hours to the point of disappearance of the purple color or leaving a permanent stain.

Bentonite has several advantages in this paper-based meat spoilage detection detector: It is inexpensive. It has a small particle size, is highly porous, and has a high surface area. This allows it to adsorb large amounts of the dye and also permits easy access of the TVB-N compounds to the dye. Similarly, it has a high cation exchange capacity, which facilitates reaction of the TVB-N compounds with the dye. Bentonite is impermeable and highly viscous when suspended in water. Because of its structure and morphology, bentonite also has a high gas absorption capacity.

An important feature of the matrix formulation is the interaction between carboxyl groups in the binder and metal cations in the clay pigment. While soybean hull and bentonite are the preferred binder and clay pigment, respectively, the matrix components are not limited to bentonite and soyhull. Other clay pigments and other binders having similar structural and functional properties may also be used. Any clay pigment may be used. Mineral clays of smectite group including the dioctahedral minerals montmorillonite, beidellite, and nontronite, and the trioctahedral minerals hectorite (Li-rich), saponite (Mg-rich), and sauconite (Zn-rich) are some of the preferred alternatives for bentonite. Similarly, soybean hull in the binder can be replaced by other carboxyl group-rich feedstock materials such as citrus peel, sugar beet pulp, apple pomace, and carboxylated cellulose fibers (e.g. CMC, TEMPO-oxidized nanocellulose, and the like).

The sensitivity the meat spoilage detector described above was evaluated by exposing the detectors to samples of from 5 μL to 100 μL of 1 mM ammonium hydroxide solution. The colorimetric change at each concentration was recorded. The durability of the colorimetric change—how long the color change remains on each detector was tested by exposing each detector to 100 μL of 5 mM ammonium hydroxide solution. This drives a definite color change in each detector. The time is then recorded for how long it takes the color change to fade.

Initial Results:

Two samples of each gas detector were prepared at each test point (i.e. for each detector with a different coating formulation and coat weights). One detector in each pair was maintained at 4° C. (the accepted temperature for meat refrigeration). The other detector in each pair was maintained at room temperature to mimic temperature abuse conditions. The results are shown in Tables 3 and 4.

TABLE 3

Test Results-Soybean Hull (SBH)

| Coating | Sensitivity (1 mM, μL) | Durability (Room) (hours) | Durability (Fridge) (hours) | Coat Weight (g/m$^2$) |
|---|---|---|---|---|
| CSP-1 bentonite + SBH 6 | 25 | 2.5 | 12 | 8.57 |
| CSP-1 bentonite + SBH 15 | 25 | 2.5 | 12 | 9.07 |
| CSP-1 bentonite + SBH 15 & 15 | 25 | 9 | 24 | 20.16 |
| CRD-O bentonite + SBH 6 | 25 | 2 | 9 | 9.07 |
| CRD-O bentonite + SBH 15 | 25 | 3 | 9 | 11.59 |
| CRD-O bentonite + SBH 15 & 15 | 50 | 9 | 24 | 22.68 |
| Control Bent/SBH 6 | 50 | 2 | 4 | 8.06 |
| Control Bent/SBH 15 | 50 | 2 | 4 | 8.57 |
| Control Bent/SBH 15 & 15 | 50 | 5 | 12 | 11.59 |

TABLE 4

Sensitivity and Durability

| Coating | Sensitivity (1 mM, μL) | Coat Weight (g/m$^2$) |
|---|---|---|
| SBH Liq/CSP 1 | 50 | 19.16 |
| SBH Liq/CSP 2 | 100 | 27.54 |
| SBH NFC/CSP 1 | 50 | 4.79 |
| SBH NFC/CSP 2 | 100 | 12.57 |
| SBH NFC (10 parts)/CSP 1 | 15 | 10.18 |
| SBH NFC (10 parts)/CSP 2 | 25 | 19.76 |

Real-Time Gas Detector Testing:

To test the detectors using real food products, catfish fillets were cut to equal sizes and spread homogenously into petri dishes. Daily bacterial growth in each sample was monitored using aerobic bacterial count. Identification of spoilage bacteria was done in conventional fashion by measuring fatty acid methyl esters via gas chromatography. See Sasser, M. (2006) "Bacterial identification by gas chromatographic analysis of fatty acids methyl esters (GC-FAME)," published by MIDI Labs, Inc, 125 Sandy Drive, Newark, Del., U.S.A.)

Figure 2:
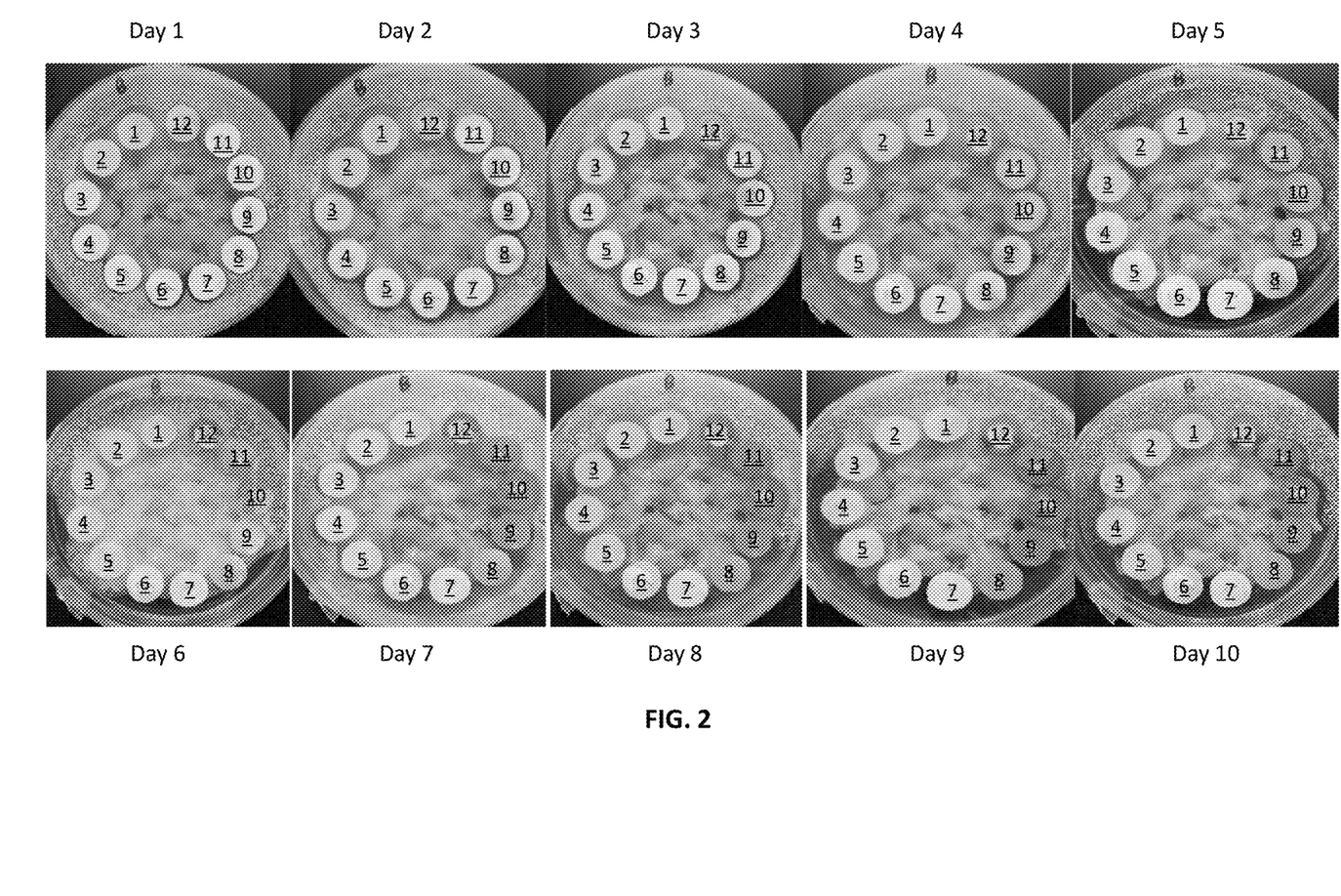
FIG. 2 shows a series of daily pictures of samples taken over a 10-day period showing activation time (color change is from yellow to blue) of detectors B: CSP+full soybean hull with pH ranging from pH: 0.25 (detector 1) to pH: 5.2 (detector 12).

Referring now to FIG. 2, the response of gas detectors at 12 different pH values ranging from pH 0.25 (detector 1 in FIG. 2) to pH 5.2 (detector 12 in FIG. 2) to meat spoilage was recorded in a daily simply by taking photographs. Each of the detectors was fabricated as noted in the working example. As can be seen in FIG. 2, only minor colorimetric changes are seen in Days 1, 2, and 3. But by Day 4 and Day 5, detectors 9 through 12 are noticeable changed toward purple. By Day 6, detectors 8 through 12 are noticeable changed toward purple. The effect is pronounced by Day 7 and remains unchanged through the Day 10. Detectors 8-12 showed a distinct and lasting colorimetric change in response to spoliation of the fish.

Figure 3:
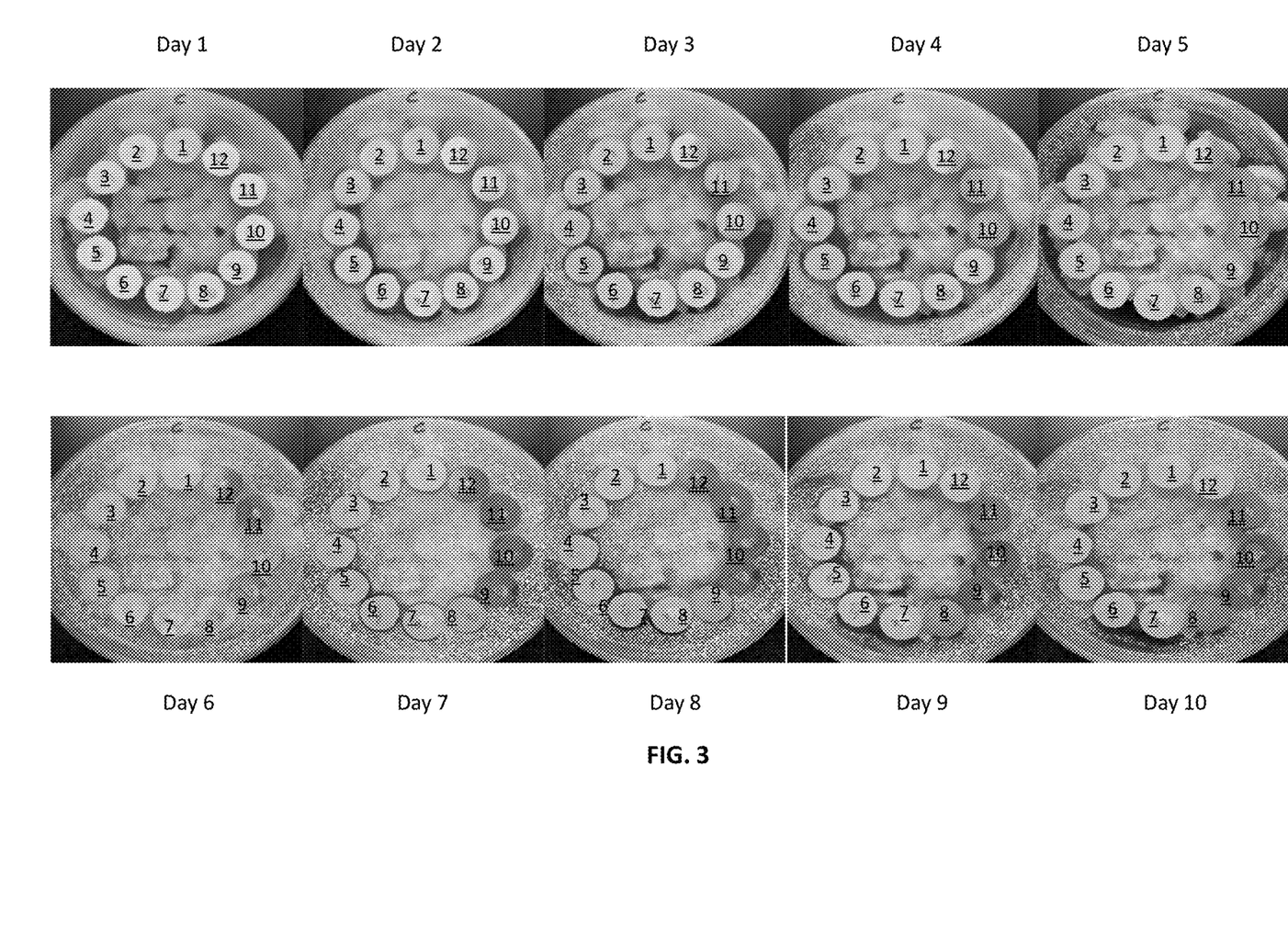
FIG. 3 shows a series of daily pictures of samples taken over a 10-day period showing activation time (color change is from yellow to purple) of gas detectors: Bentonite+NF Processed SBH with pH ranging from pH: 0.25 (detector 1) to pH: 5.2 (detector 12).

FIG. 3 shows the results of parallel test using detectors comprising nano-fibrillated, processed soybean hull (NFSBH) as the binder. In the same fashion as in FIG. 2, minor colorimetric changes are seen in detectors 10, 11, and 12 at Day 3. By Day 4 the color change in detectors 9, 10, 11, and 12 is pronounced, and remains so through Day 10.

FIGS. 2 and 3 together show that the pH level of the detector correlates with the stage of microbial growth in the fish samples. The correlation of the detectors' pH level with the stage of microbial growth showed that activation of each detector is delayed with decreasing pH level, regardless of the type of the detector. Initially all detectors were yellow. As spoilage progressed with increasing microbial activity and storage time, more detectors with lower pH levels were activated. The color change occurred in detectors 10, 11, and 12 almost always at the same day with decreasing pH of the detectors for both Detector B (SBH and bentonite) and Detector C (NFSBH+bentonite). However, the tone of the purple was significantly sharper and more vibrant with Detector C. This is due to increased porosity and increased gas capturing ability of bentonite particles per unit of detector surface. Using soybean hull nano-fibrillated cellulose as part of the binder system reduced the binder demand of the detector coating from 25 parts to 10 parts. This increased the overall porosity and gas capturing ability of the detector. At lower binder usage fewer numbers of bentonite particles are blocked by soybean hull binder components. This is thought to enhance the ability of bentonite to capture and hold more of the total volatile basic compounds (the product of spoilage bacteria).

The sensory response of NFSBH-containing detectors with initial pH values ranging from 0.25-5.20 is presented as digital images in FIG. 3. One of the obstacles for commercialization of optical detectors is the misleading signals, i.e., false negatives and false positives. Disclosed herein is a freshness and spoilage detector that can be tailored for varying meat weight and packaging headspace so that regardless of these packaging variables, the detector correctly shows the freshness level and spoilage time of the meat products.

For the 60 g fish meat sample with 160 cm$^3$ packaging headspace volume, activation of NFSBH-based detectors and the resultant color change, from yellow to purple, starts at the second day of storage with detector #12 (pH: 5.20) and progresses to the detector #11 (pH: 4.50) and #10 (pH: 4.00) on the third day. On the 5th day, detector #9 (pH: 3.50) activates and, finally, on the spoilage day (day 9 in this study according to the TVC limit shown in FIG. 1), detector #8 (pH: 3.00) changes color. It is observed that none of the NFSBH-detectors are activated on the first day of storage, indicating the freshest state of fish meat in the packaging. The detectors with decreasing pH start to turn purple as the meat product is experiencing freshness deterioration until the point of spoilage, shown by the activation of detector #8 on day 9. The purple color intensity could be fine-tuned by slightly increasing its pH between 3.00 and 3.50 for the tested meat weight.

The detectors composed of NFSBH binders were further analyzed for their sensory response under two different packaging conditions: I) increased sample size (fish weight), II) increased packaging size (available headspace air volume).

Figure 4:
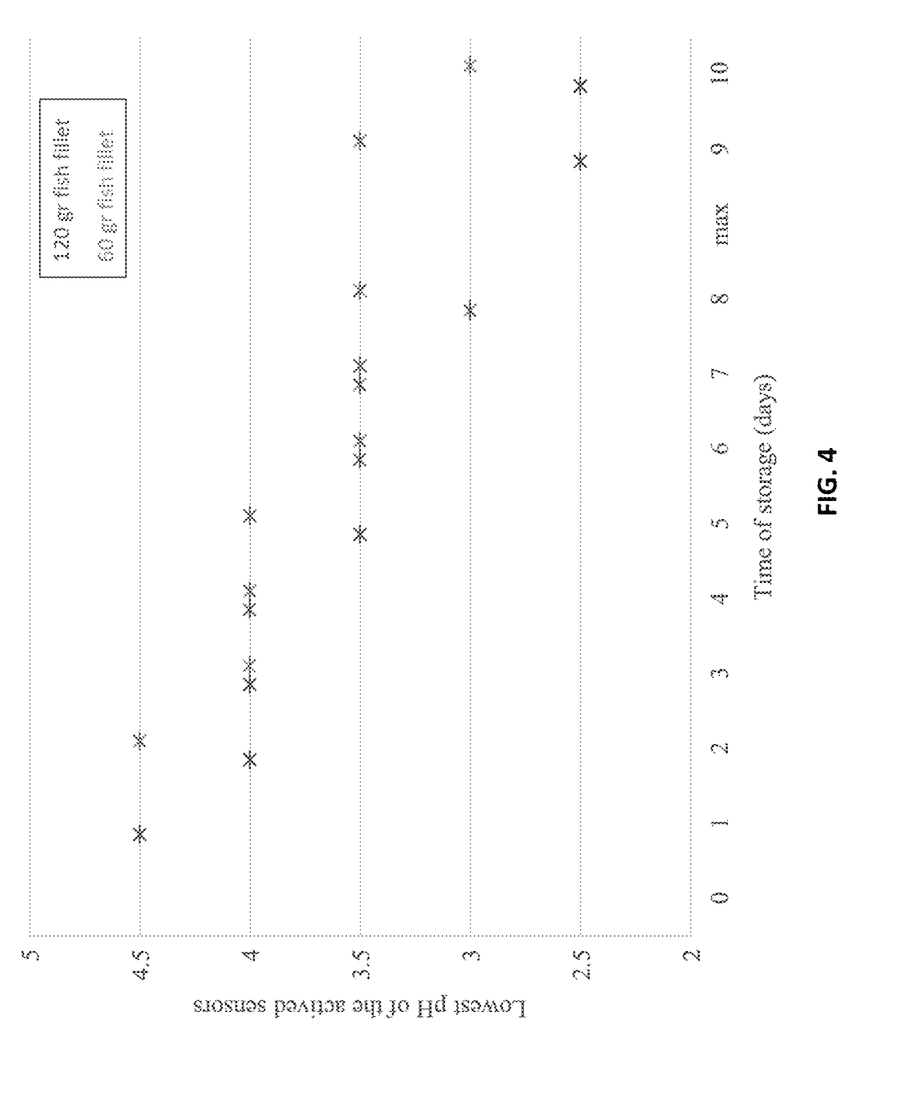
FIG. 4 is a graph showing the effect of fish weight (120 g fillet, blue x's vs. 60 g fillet, orange x's) on detector response. X-axis shows storage time in days. Y-axis shows lowest pH of the activated detectors.

Effect of Fish Weight and Headspace Between Food and Detector:

A series of detectors as described above were made to see if there was a correlation between the amount of fish being tested and pH of the detectors. See FIGS. 4, 5A, and 5B. Here, the samples and detectors were arranged as in FIGS. 2 and 3, but the two sample sets had either a 120 g fish fillet sample (blue x's in FIG. 4) or a 60 g fish fillet sample (orange x's in FIG. 4). FIG. 4 shows the results over the course of a 10-day study. For the 120 g fish fillets, the lowest pH of the activated detector was 2.5 (at Day 9). For the 120 g fish fillets, the lowest pH of the activated detector was 3.0

Figure 5A:
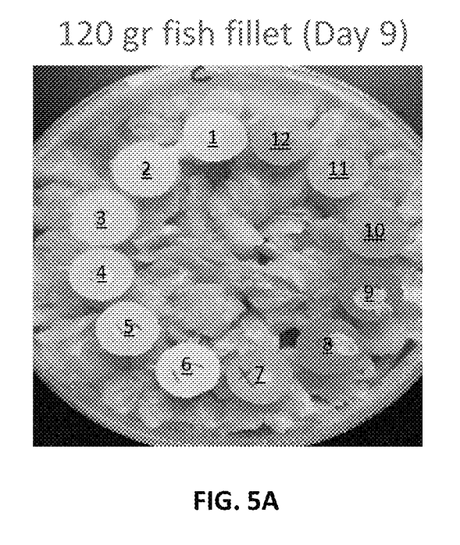
FIG. 5A is a photograph of the 120 g fillet (and detectors 1 to 12) from FIG. 4 at Day 9.
Figure 5B:
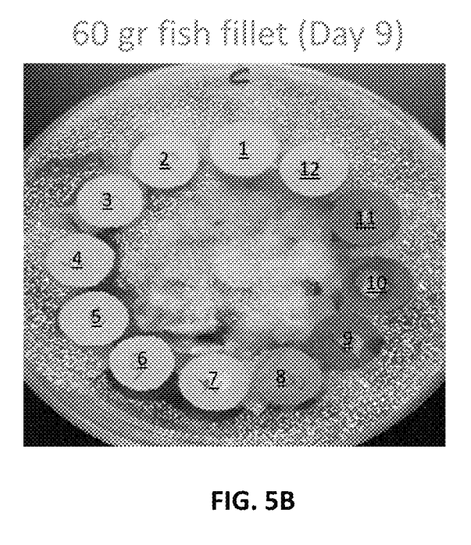
FIG. 5B is a photograph of the 60 g fillet (and detectors 1 to 12) from FIG. 4 at Day 9.

FIGS. 5A and 5B are photographs of the two studies at Day 9. FIG. 5A is a photograph of the 120 g fillet (and detectors 1 to 12) at Day 9. FIG. 5B is a photograph of the 60 g fillet (and detectors 1 to 12) at Day 9. As can be seen from these two figures, the color change is unmistakable. In FIG. 5A, compare the color of detectors 1-6 (unmistakably yellow) to detectors 7-12 (unmistakably purple). In FIG. 5B, which depicts the results for the smaller sample size, detectors 9, 10, and 11, are quite clearly purple on Day 9. Activation of detectors started earlier in the time of storage with the 120 g fish samples than in the 60 g fish samples. Also, more detectors with lower pH levels were activated at the 9th day of the storage in the 120 g fish samples. This is surely due to the increased mass fish flesh in the 120 g samples, which supports an increased amount of microbial activity, which in turn generates an increased amount of TVB-N to activate the detectors with lower pH levels.

Figure 6:
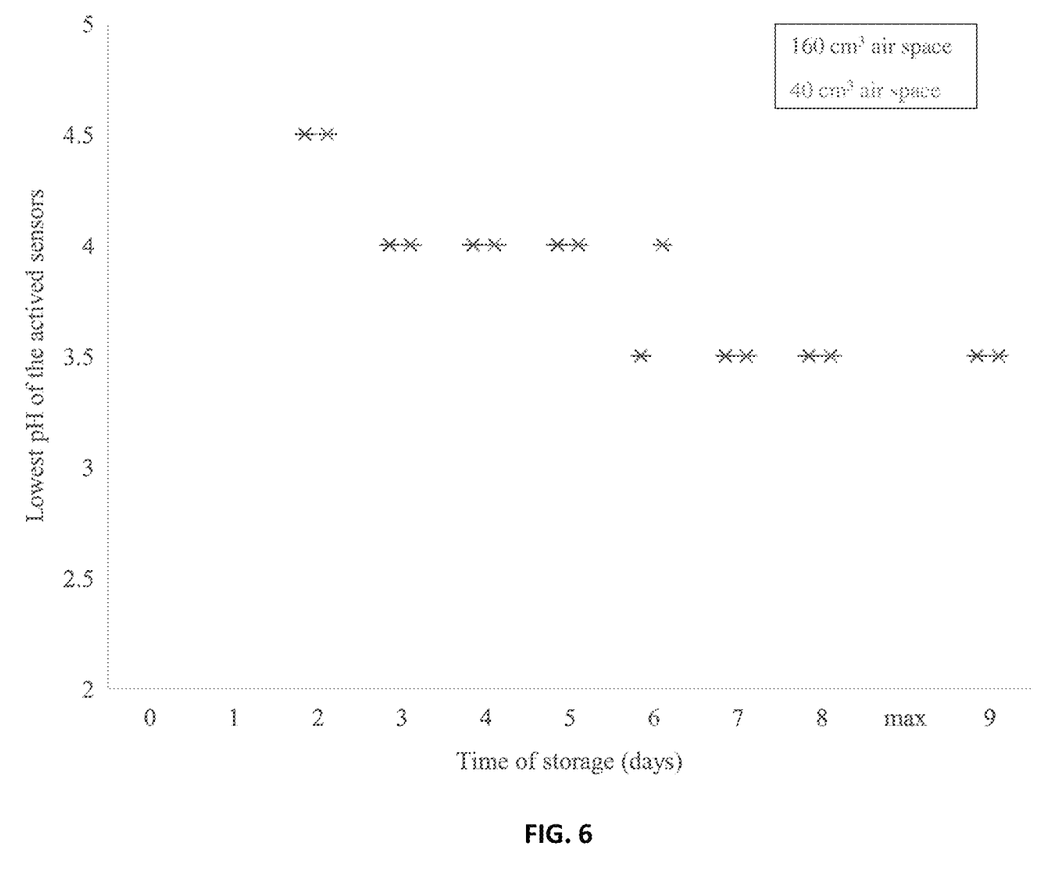
FIG. 6 is a graph showing the effect of headspace (160 cm³, blue x's vs. 40 cm³, orange x's) on detector response. X-axis shows storage time in days. Y-axis shows lowest pH of the activated detectors.
Figure 7A:
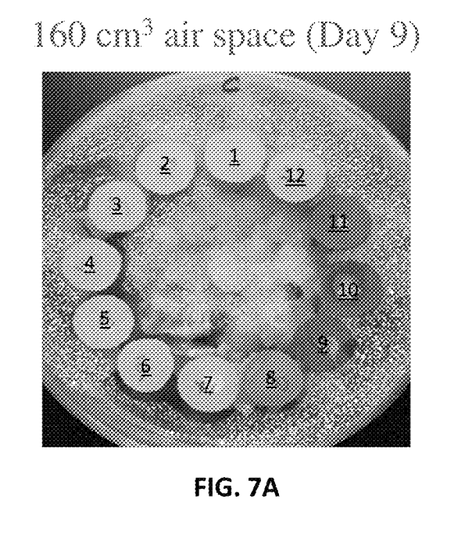
FIG. 7A is a photograph of the 160 cm³ headspace fillet (and detectors 1 to 12) from FIG. 6 at Day 9.
Figure 7B:
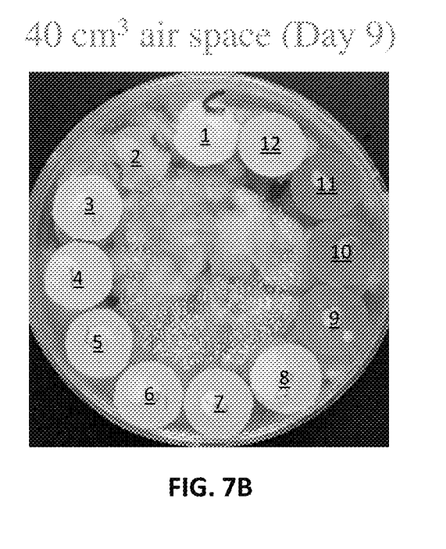
FIG. 7B is a photograph of the 40 cm³ headspace fillet (and detectors 1 to 12) from FIG. 6 at Day 9.

The fish weight study shows that using 120 g of fish fillet samples (FIG. 4; blue marks), as opposed to 60 g (FIG. 4; orange marks) would affect the activation (color change onset) time and pH. Increasing fish weight leads to an earlier color change in the detectors of the same initial pH. In addition to the activation time, an increase in the fish weight and higher TVBN emission associated with it causes a downward shift in the optimum pH range from 3.00-3.50 (for 60 g) to 2.50-3.50 (for 120 g) for the studied fish meat weights. The lower limit of this range is representative of the "spoilage detector" ($9^{th}$ day, according to TVC), changing color on the spoilage day of the fish fillets. Meanwhile, the upper limit represents the suitable detector for showing the "freshness deterioration onset" ($5^{th}$ day, according to TVC). The other detectors, with the initial pH falling between these two extreme ends, show the gradual decrease in the food quality and represent real-time freshness monitoring detectors. See FIGS. 5A and 5B. These findings indicate that it is possible to customize the optimal pH range of detectors to provide quality monitoring in larger or smaller sample sizes. At higher sample weights, detectors of lower pH values would be needed for freshness and spoilage detection. The pH of novel detectors can virtually be adjusted all the way down to zero, covering all the packaged meat weights available in the markets FIGS. 6, 7A, and 7B show results for an analogous test, this time testing the response of the detectors as a function of headspace (i.e., the volume of airspace between the detectors and the meat sample). FIG. 6 shows the results over the course of a 10-day study. For both the 160 cm$^3$ headspace samples (blue x's in FIG. 6) and the 40 cm$^3$ headspace samples (orange x's), the lowest pH of the activated detector was 3.0

FIGS. 7A and 7B are photographs of the two headspace studies at Day 9. FIG. 7A is a photograph of the 160 cm$^3$ headspace samples (and detectors 1 to 12) at Day 9. FIG. 7B is a photograph of the 40 cm$^3$ headspace samples (and detectors 1 to 12) at Day 9. As can be seen from these two figures, the color change is unmistakable. In FIG. 7A, compare the color of detectors 1-8 and 12 (unmistakably yellow) to detectors 9-11 (unmistakably purple). In FIG. 7B, which depicts the results for the smaller headspace samples, the results are essentially identical.

As seen in FIGS. 7A and 7B, headspace had essentially no impact on the results. Regardless of the different headspace, similar amounts of fish activated the same detectors numbers (9, 10, and 11), indicating that headspace does not significantly impact the activity of the detectors. Detector 11 (pH 4.5) was activated on Day 2 of storage regardless of the air space. By Day 7, detectors of pH 3.5 were activated. See FIG. 6.

Referring collectively to FIGS. 6, 7A, and 7B, exposing the detectors to the same amount of fish should generate the same amount of TVBN compounds in both Petri dishes. The headspace air volume in the studied range (40 and 160 cm$^3$) and the given packaging conditions have no significant impact on the sensory response of the tested detectors. The reason is that the TVBN compounds would keep their upward movement until they contact, attach to, and accumulated on the detector's surface rather than spreading out in the available volume at the headspace. Furthermore, the oxygen amount within the headspace was adequate for the spoilage bacteria to thrive for both samples since the spoilage of the fish meat occurred simultaneously. Therefore, no effect of headspace in the fish packaging for freshness and the spoilage of the fish samples was seen within the studied range.

The SBH-containing detectors were also evaluated for their time and pH-dependent sensory response under fixed and varied packaging conditions (data not shown). Since the corresponding detector responses were similar to the NFSBH-containing detectors and application of NFSBH resulted in more vibrant colors, only NFSBH data are presented. Appearance of brighter colors can be attributed to the improved BCP dye immobilization on the coating surface as a result of higher surface area in the NFSBH binder due to fiber defibrillation. Additionally, emitted TVBGs are better entrapped on the more porous tortuous coated surface due to reduced binder demand with fiber defibrillation. Nanofibrillation in this study lowered the binder demand in coating formulation from 25 to 10 parts.

Sensitivity and Durability:

The results of daily responses of detectors to the fridge-stored fish samples, presented in the last section, show that the best initial pH value in the studied range (i.e., 0.25 to 5.20), with regards to its correlation to the quality deterioration and spoilage of fish samples for 60 gr fish weight, is about 3.00. Therefore, these detectors were tested for durability determination. See Table 5:

TABLE 5

Sensitivity and durability of SBH- and NFSBH-based detectors (pH: 3.00)

| Binder Type | Sensitivity (1 mM, µL) | Durability (Room)(hr) | Durability (Fridge)(hr) | Coat Weight (g/m$^2$) |
|---|---|---|---|---|
| SBH | 100 | 12 | 24 | 21.19 |
| NFSBH | 50 | 12 | 24 | 19.76 |

The durability at room temperature and fridge are the same, 12 and 24 hours, respectively, indicating that the durability not affected by binder nanofibrillation and is mainly attributable to bentonite's platelet structure. The tortuous path provided by porous interlayer spaces in the structure of bentonite increases the mean gas diffusion length and entraps the absorbed ammonia in the detector matrix. The gas impermeability of the detectors might contribute to the shelf life extension of the packaged food products by reducing the water vapor permeability, especially if combined with modified atmosphere packaging (MAP) technologies. It is worth noting that once the color change takes place in a detector it will not get back to its original appearance even after several days. This irreversibility of the color change makes the developed detectors suitable for providing useful information about the food product's history during the handling, transportation, and distribution stages of the food supply chain.

Conclusion:

The novel paper-based colorimetric detector developed in this study is manufactured using an easy-to-apply and scalable coating method by incorporating a biodegradable and low-cost SBH-bentonite matrix for immobilization of sensor array (i.e., BCP dye). Availability of hydrophobic, hydrophilic, anionic, and cationic reaction sites on the SBH binder, platelet structure of bentonite, and its interlayer cations led to stronger physical and chemical interactions among SBH, bentonite, and paper. The resultant compact matrix provides effective dye-immobilization, minimized dusting of the coating mixture, and improved gas adsorption capacity. Fabrication of the detectors with a wide range of initial pH values (0.25-5.20) and exposing them to aerobically stored catfish fillets at chilled temperature (4° C.) showed that the detectors of different initial pH change color at different storage days. The activation time can be correlated with daily quantified microbial growth (TVC), providing a set of detectors covering the optimum pH range suitable for the detection of freshness level and spoilage.

Nanofibrillation of the binder enhanced the color vibrancy and had no significant effect in the sensory response of the detectors. The stability of color change and irreversibility of the activated detectors make them capable of giving information on the history of the food product during different stages of the food supply chain. Investigating the effect of changes in fish weight and packaging headspace showed that the developed detectors can be tailored for a wide range of sample and packaging sizes by simply adjusting the pH of the detector. The novel real-time detector is inexpensive and can detect freshness level and spoilage in the form of an on-package detector, thereby reducing unnecessary food wastage and ensuring customers' wellness.

What is claimed is:

1. A device for detecting volatile compounds, the device comprising:
    a substrate;
    a matrix disposed on the substrate, the matrix comprising
        a binder comprising carboxyl-containing biomass
        a clay; and
        a pH-sensitive indicator dye admixed with the binder and the clay;
    wherein the pH-sensitive indicator dye is used in a concentration that allows the pH-sensitive indicator dye to change color in response to contact with a concentration of a volatile compound.

2. The device of claim 1, wherein the clay comprises a smectite clay.

3. The device of claim 1, wherein the clay comprises an illite clay.

4. The device of claim 1, wherein the clay comprises a phyllosilicate.

5. The device of claim 1, wherein the clay comprises bentonite.

6. The device of claim 1, wherein the binder comprises cellulosic biomass.

7. The device of claim 6, wherein the binder comprises a material selected from the group consisting of soybean hulls, acid-treated soybean hulls, and nanofibrillated soybean hulls.

8. The device of claim 1, wherein the pH-sensitive indicator dye is used in a concentration that allows the device to detect volatile bases.

9. A device for detecting volatile basic compounds, the device comprising:
    a substrate;
    a matrix disposed on the substrate, the matrix comprising
        a binder comprising acid-treated soybean hulls;
        a smectite clay; and
        a pH-sensitive indicator dye admixed with the binder and the smectite clay;
    wherein the pH-sensitive indicator dye is used in a concentration that allows the pH-sensitive indicator dye to change color in response to contact with a pre-determined concentration of a volatile basic compound.

10. The device of claim 9, wherein the clay comprises bentonite.

11. The device of claim 9, wherein the clay comprises bentonite and the binder comprises nanofibrillated soybean hulls.

12. The device of claim 9, wherein the substrate is a material selected from the group consisting of paper, thermoplastic films, thermosetting films, and cellulosic films.

13. The device of claim 9, wherein the pH-sensitive indicator dye is selected from the group consisting of Bromocresol Purple, dichlorofluorescein, Methyl Red, Bromocresol Green, and Chlorophenol Red.

14. A method for showing freshness and testing spoilage of food, the method comprising
    (a) providing a device comprising:
    a substrate;
    a matrix disposed on the substrate, the matrix comprising
        a binder comprising carboxyl-containing biomass;
        a clay; and
        a pH-sensitive indicator dye admixed with the binder and the clay;
    wherein the pH-sensitive indicator dye is used in a concentration that allows the pH-sensitive indicator dye to change color in response to a concentration of total volatile base nitrogen compounds generated by spoilage microorganisms growing within a food product; and
    wherein the change in color of the pH-sensitive indicator dye occurs at or below a threshold concentration of spoilage microorganisms within the food product at which the food product is deemed unsafe to consume by humans; and
    (b) placing the device of step (a) in a package of food.

15. The method of claim 14, wherein the clay comprises a smectite clay.

16. The method of claim 14, wherein the clay comprises an illite clay.

17. The method of claim 14, wherein the clay comprises a phyllosilicate.

18. The method of claim 14, wherein the clay comprises bentonite.

19. The method of claim 14, wherein the binder comprises a material selected from the group consisting of soybean hulls, acid-treated soybean hulls, and nanofibrillated soybean hulls.

* * * * *